United States Patent

Lin

[11] Patent Number: 6,056,621
[45] Date of Patent: May 2, 2000

[54] HULA HOOP

[76] Inventor: Ruey-Hsiung Lin, No. 11-1, Chung Su Rd., Koou, Tatu Hsiang, Taichung Hsien, Taiwan

[21] Appl. No.: 09/328,185

[22] Filed: Jun. 9, 1999

[51] Int. Cl.[7] .................................................. A63H 33/02
[52] U.S. Cl. ......................... 446/236; 446/129; 482/131; 601/132
[58] Field of Search .............................. 446/28, 129, 236; 482/110, 131; 601/132

[56] References Cited

U.S. PATENT DOCUMENTS

| 4,052,982 | 10/1977 | Ozeryansky | 446/236 X |
| 4,215,510 | 8/1980 | Worrell | 446/28 |
| 4,380,885 | 4/1983 | Komagata | 446/236 |
| 5,492,526 | 2/1996 | Chen | 601/132 |
| 5,531,665 | 7/1996 | Chen | 601/132 X |
| 5,997,449 | 12/1999 | Lee | 482/131 |

Primary Examiner—John A. Ricci
Attorney, Agent, or Firm—Rosenberg, Klein & Lee

[57] ABSTRACT

A hula hoop includes a spheres connected by a circular wire and each sphere has two recesses so that two magnets are received in the two recesses of the sphere. The wire has two ends which are securely connected with each other by an end member which is received in a spherical casing. The two magnets extend out from the outside of each sphere.

4 Claims, 3 Drawing Sheets

HULA HOOP

FIELD OF THE INVENTION

The present invention relates to a hula hoop, and more particularly, to an improved hula hoop which includes a plurality of spheres connected by a circular wire and each sphere has two magnets embedded to the outside thereof.

BACKGROUND OF THE INVENTION

A conventional hula hoop generally includes two semi-circular members which are connected with each at two ends thereof so as to become a hoop. The conventional hula hoop is a solid loop so that the hula hoop only contacts the body of the user at one point. The single contact point is not enough to provide the user a better massage feature. Accordingly, an improved hula hoop is developed and has a plurality of protrusions extending radially inward from the inside of the hula hoop. Although the protrusions provide a massage feature, the contact point is still limited and the shortcoming of the conventional hula hoop is still not resolved.

The present invention intends to provide a hula hoop which includes a plurality of spheres connected by a circular wire and each sphere has two magnets embedded therein so that when using the hula hoop, the spheres will move along the wire and more than one sphere will contact the user's body.

SUMMARY OF THE INVENTION

In accordance with one aspect of the present invention, there is provided a hula hoop comprising a wire extending through a plurality of spheres and the wire having two ends connected by an end member. Each sphere has at least one recess defined therein and each recess receives a magnet therein.

The object of the present invention is to provide a hula hoop which has a plurality of spheres and each sphere has two magnets embedded therein so that when using the hula hoop, more than one sphere will contact the user's body to provide a better massage feature.

Further objects, advantages, and features of the present invention will become apparent from the following detailed description with appropriate reference to the accompanying drawings.

DETAILED DESCRIPTION OF THE PREFERRED EMBODIMENT

Figure 1:
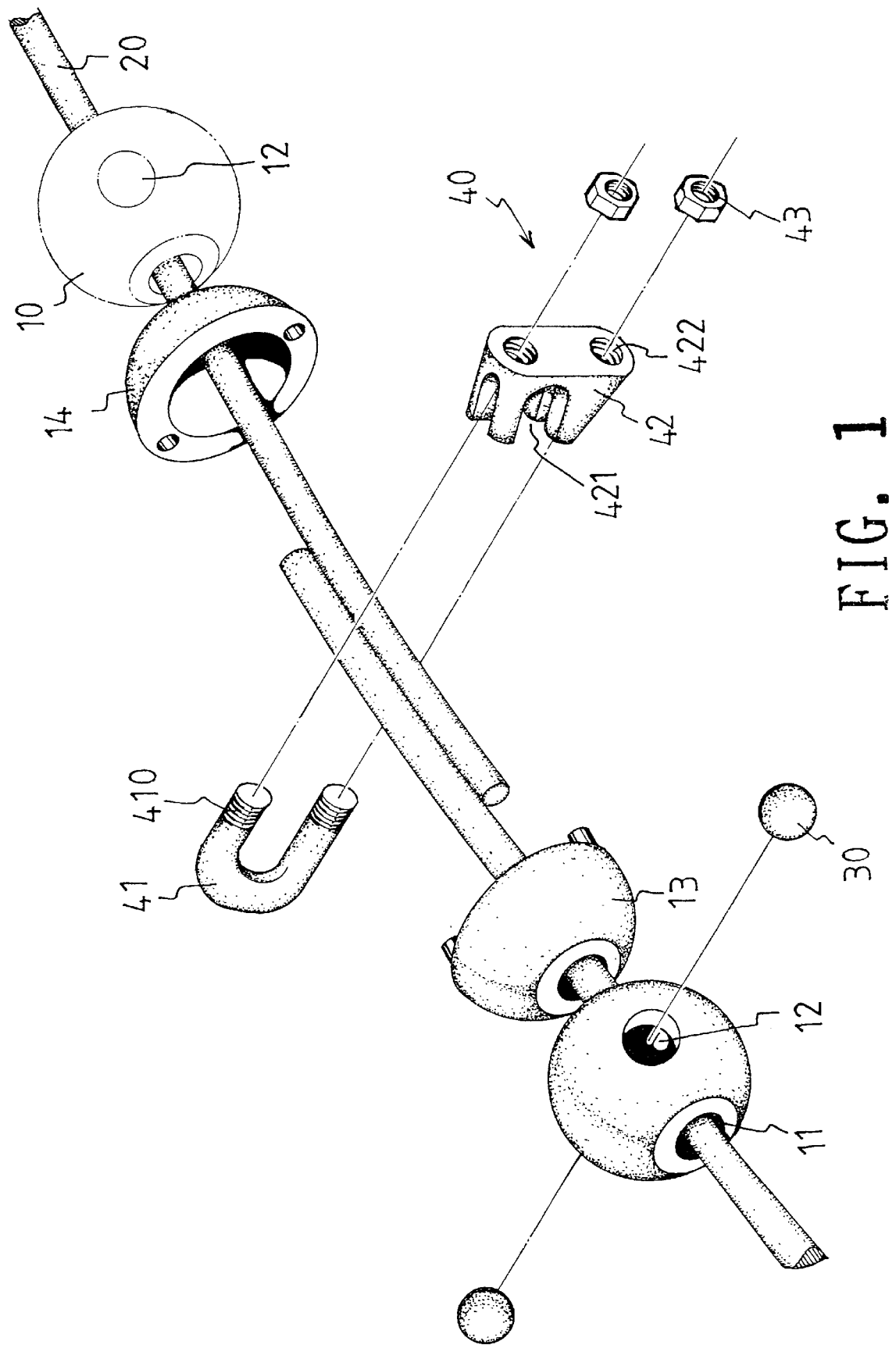
FIG. 1 is an exploded view of the hula hoop in accordance with the present invention.
Figure 2:
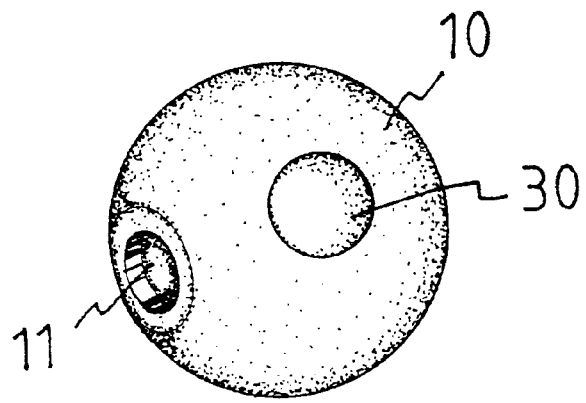
FIG. 2 is a perspective view of the sphere of the hula hoop in accordance with the present invention.
Figure 3:
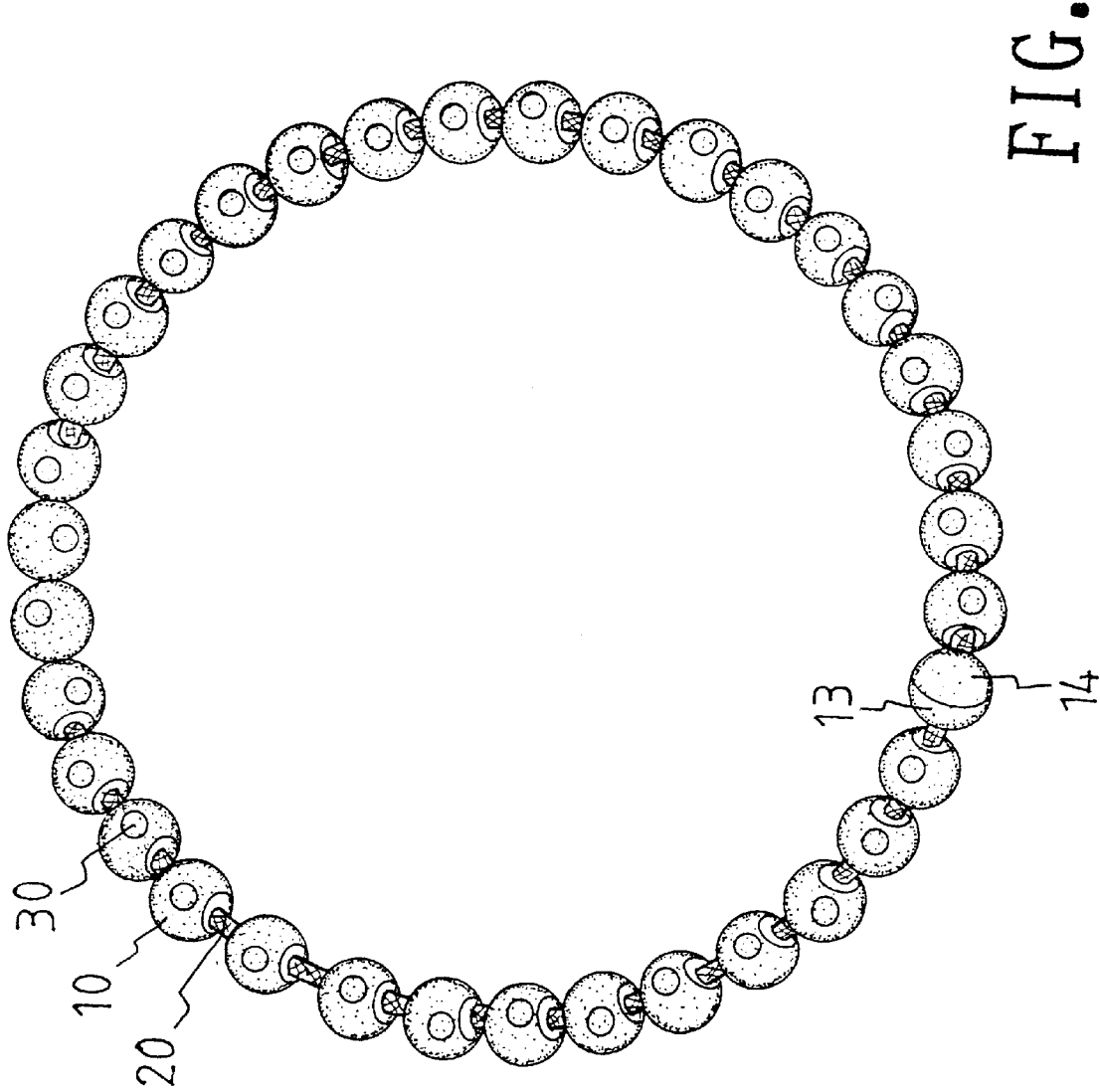
FIG. 3 is a perspective view of the hula hoop in accordance with the present invention.

Referring to FIGS. 1 to 3, the hula hoop in accordance with the present invention comprises a wire (20) having two ends connected by an end member (40) and a plurality of spheres (10) connected by the wire (20). Each sphere (10) has a passage (11) defined therethrough for the wire (20) extending through the passage (11). Each sphere (10) has two recesses (12) defined therein and each recess (12) receives a magnet (30) therein, wherein each magnet (30) extends radially outward from the outside of the sphere (10).

The end member (40) includes a block (42) having two holes (422) and a recess (421) respectively defined therein. The recess (421) communicates with the two holes (422). The two ends of the wire (20) are received in the recess (421). A U-shaped member (41) has two threaded ends (410) and the two ends of the wire (20) are retained in the U-shaped member (41). The two threaded ends (410) extend through the two holes (422) and are engaged with two nuts (43) so that the two ends of the wire (20) are securely clamped by the U-shaped member (41) and the block (42).

A spherical casing composed a first half (13) and a second half (14) receives the end member (40).

Figure 4:
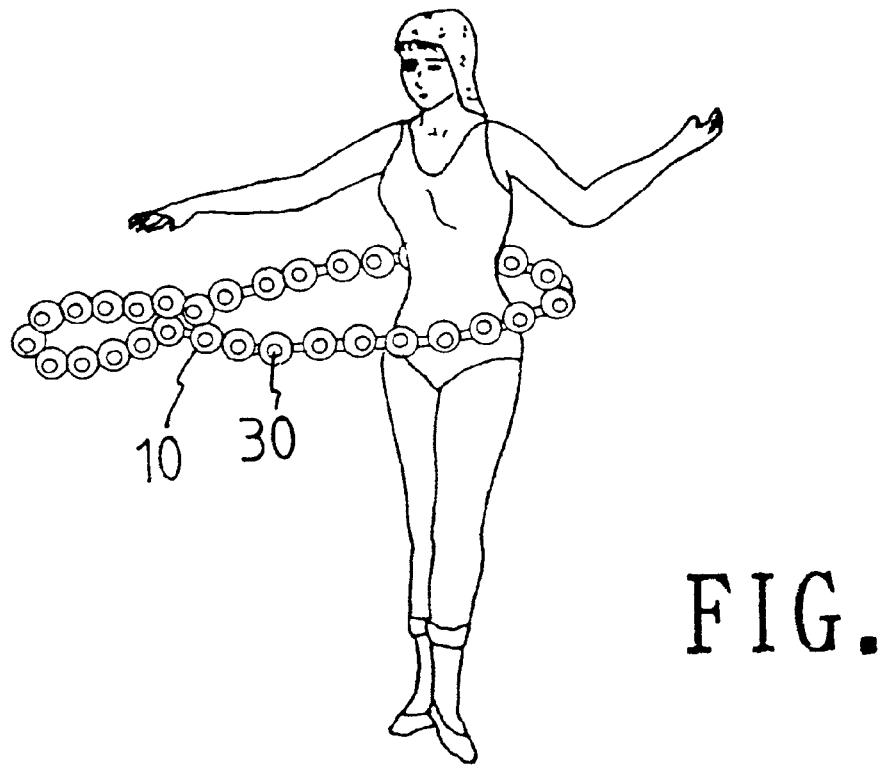
FIG. 4 is an illustrative view to show a user using the hula hoop of the present invention.

It is to be noted that the spheres (10) are movable on the wire (20) so that when using the hula hoop as shown in FIG. 4, more than one sphere (10) will contact the user's body and the magnets (30) provide a better massage feature.

The invention is not limited to the above embodiment but various modifications thereof may be made. It will be understood by those skilled in the art that various changes in form and detail may be made without departing from the scope and spirit of the present invention.

What is claimed is:

1. A hula hoop comprising:

a wire (20) having two ends connected by an end member (40), and a plurality of spheres (10) each having a passage (11) defined therethrough, said wire (20) extending through said passage (11) of each sphere (10), each sphere (10) having at least one recess (12) defined therein and each recess (12) receiving a magnet (30) therein.

2. The hula hoop as claimed in claim 1, wherein each magnet (30) extends radially outward from the outside of said sphere (10).

3. The hula hoop as claimed in claim 1, wherein said end member (40) includes a block (42) having two holes (422) and a recess (421) respectively defined therein, said recess (421) communicating with said two holes (422), the two ends of said wire (20) received in said recess (421), a U-shaped member (41) having two threaded ends (410) and the two ends of said wire (20) retained in said U-shaped member (41), said two threaded ends (410) extending through said two holes (422) and engaged with two nuts (43).

4. The hula hoop as claimed in claim 1 further comprising a spherical casing in which said end member (40) is received.

* * * * *